United States Patent
Arnold et al.

(10) Patent No.: US 11,859,023 B2
(45) Date of Patent: Jan. 2, 2024

(54) SYNTHESIS OF UNIFORMLY DEFINED MOLECULAR WEIGHT MANNOSYLATED DEXTRANS AND DERIVATIVES THEREOF

(71) Applicant: Navidea Biopharmaceuticals, Inc., Dublin, OH (US)

(72) Inventors: Jeffrey Arnold, Andover, MA (US); David A. Ralph, Columbus, OH (US)

(73) Assignee: Navidea Biopharmaceuticals, Inc., Dublin, OH (US)

( * ) Notice: Subject to any disclaimer, the term of this patent is extended or adjusted under 35 U.S.C. 154(b) by 0 days.

(21) Appl. No.: 17/370,920

(22) Filed: Jul. 8, 2021

(65) Prior Publication Data

US 2022/0010036 A1  Jan. 13, 2022

Related U.S. Application Data

(60) Provisional application No. 63/049,485, filed on Jul. 8, 2020.

(51) Int. Cl.
  *C08B 37/02* (2006.01)
  *A61K 51/06* (2006.01)

(52) U.S. Cl.
  CPC ........ *C08B 37/0021* (2013.01); *A61K 51/065* (2013.01)

(58) Field of Classification Search
  CPC .................................................. C08B 37/0021
  See application file for complete search history.

(56) References Cited

U.S. PATENT DOCUMENTS

| | | | |
|---|---|---|---|
| 6,409,990 B1 * | 6/2002 | Vera | A61K 51/065 424/9.4 |
| 2004/0072761 A1 | 4/2004 | Campbell et al. | |
| 2012/0213700 A1 | 8/2012 | Magneson et al. | |
| 2015/0023876 A1 | 1/2015 | Cope et al. | |
| 2017/0209584 A1 | 7/2017 | Schlesinger et al. | |
| 2018/0099048 A1 | 4/2018 | Cope | |

FOREIGN PATENT DOCUMENTS

| | | |
|---|---|---|
| WO | 2015013341 A1 | 1/2015 |
| WO | 2016011415 A2 | 1/2016 |
| WO | 2016011419 A1 | 1/2016 |
| WO | 2016118188 A1 | 7/2016 |

OTHER PUBLICATIONS

Anelli et al., "L-Glutamic Acid and L-Lysine as Useful Building Blocks for the Preparation of Bifunctional DTPA-like Ligands", Bioconjugate Chemistry, Jan. 1, 1999, pp. 137-140, vol. 10, No. 1.
Ardestani et al. "Novel and facile methods for the synthesis of DTPA-mono-amide: a new completely revised strategy in radiopharmaceutical chemistry" J Radioanal Nucl Chem, 2010, 283:447-455.
Deen et al. "Structural determinants of glomerular permeability" Am J Physiol Renal Physiol, 2001, 281: F579-F596.
Jarad et al. "Update on the glomerular filtration barrier" Curr Opin Nephrol Hypertens, May 2009 ; 18(3): 226-232.
Li et al. "Multimodal Image-Guided Enzyme/Prodrug Cancer Therapy" J. Am. Chem. Soc., 2006, 128, 15072-15073.
Movahedi et al. "Nanobody-Based Targeting of the Macrophage Mannose Receptor for Effective In Vivo Imaging of Tumor-Associated Macrophages" Cancer Res; 72(16) Aug. 15, 2012, 4177.
Sun et al. "Enhancing Tumor Penetration of Nanomedicines" Biomacromolecules. May 8, 2017; 18(5): 1449-1459.

* cited by examiner

*Primary Examiner* — Jonathan S Lau
(74) *Attorney, Agent, or Firm* — Fredrikson & Byron, P.A.

(57) ABSTRACT

Disclosed herein is method for conjugating a metal chelating agent to a functionalized dextran by reacting a chelator with an aminated dextran backbone, where the chelator comprises a one, and only one, derivatized carboxylic acid group to form a chelator-dextran complex. In certain aspects, the dextran-chelator complex is substantially free of intra- or intermolecular crosslinking. In certain aspects, the functionalized dextran is an amine dextran, an alkynyl dextran, or a thiol dextran. In exemplary implementations, the functionalized dextran is an amine dextran. In further embodiments, one and only one carboxylic acid group on the chelating agent is derivatized as a N-hydroxysuccinimide (NHS) ester.

19 Claims, 2 Drawing Sheets

SYNTHESIS OF UNIFORMLY DEFINED MOLECULAR WEIGHT MANNOSYLATED DEXTRANS AND DERIVATIVES THEREOF

CROSS-REFERENCE TO RELATED APPLICATION(S)

This application claims priority to U.S. Provisional Application No. 63/049,485 filed Jul. 8, 2020 and entitled "SYNTHESIS OF UNIFORMLY DEFINED MOLECULAR WEIGHT TILMANOCEPT AND DOTA DERIVATIVE," which is hereby incorporated by reference in its entirety under 35 U.S.C. § 119(e).

BACKGROUND OF THE INVENTION

99mTc-Tilmanocept is an FDA and EMA approved radiopharmaceutical imaging agent marketed as Lymphoseek™ for solid tumor lymphatic system mapping and guided biopsy of sentinel lymph nodes (SLNs). Tilmanocept is a dextran polymer that has been synthetically modified with amine-leashes bearing mannose and diethylenetriaminepentaacetic acid (DTPA) moieties (Compound 5a, Scheme 1). Tilmanocept is a member of a class of related molecular constructs, referred to as mannosylated dextrans, for which multiple mannose sugars and possibly other carbohydrates are attached to dextran backbones by various types of linkers or leashes. Mannosylated dextrans can be further modified with agents that provide additional functionality to the constructs. In the case of tilmanocept, the mannosylated dextran is conjugated with a chelator, DTPA, that permits tilmanocept to be labeled with various radioactive metal ions. Tilmanocept has 17±5 mannose and 3-8 DTPA moieties per 10 kDa dextran backbone. Mannosylated dextrans generally and including tilmanocept, were specifically designed to be high affinity ligands for the mannose receptor, CD206, a C-type lectin. Tilmanocept's multiple mannose moieties enable its high affinity interactions with CD206. In the case of Lymphoseek, tilmanocept is labeled with ions of 99m techetium (99mTc), a gamma emitting radioisotope with a half-life of approximately 6 hours. When injected near a tumor, Lymphoseek (99mTc-tilmanocept) enters a tumor's lymphatic drainage, whereupon it is transported to the first encountered lymph node (a SLN) and binds to CD206 displayed on the surface of macrophages residing within the SLN. Lymphoseek is used as a radiopharmaceutical imaging agent to assist cancer surgeons identify SLNs for biopsy. The starting dextran for tilmanocept (5a manufacture (Scheme 1)) is a 10 kDa average molecular weight (Mw) polymer with a typical polydispersity index (PDI) of 1.3-1.4. Construct 5a can only be achieved with PDI values approximating the starting dextran if the chemical modifications employed (Scheme 1, steps 1-4) do not result in crosslinking. Crosslinking increases polydispersity.

The current synthesis process for manufacturing tilmanocept by Scheme 1 and as previously described by Vera, et al, in U.S. Pat. No. 6,409,990 (hereinafter, the ""990 patent") has a target Mw of 15-23 kDa. However, this process is deficient in that a large proportion of tilmanocept molecules become crosslinked with other tilmanocept molecules. This crosslinking forms oligomeric species of tilmanocept which range in molecular weight from 30 to >500 kDa. Oligomerization dramatically increases the average molecular weight and polydispersity of the tilmanocept product. It is well known by those skilled in the art that, when injected into an animal or human subject, the biodistribution and pharmacokinetics of an injected substance is highly influenced by the molecular weight of the injected substance. In general, larger molecular weight

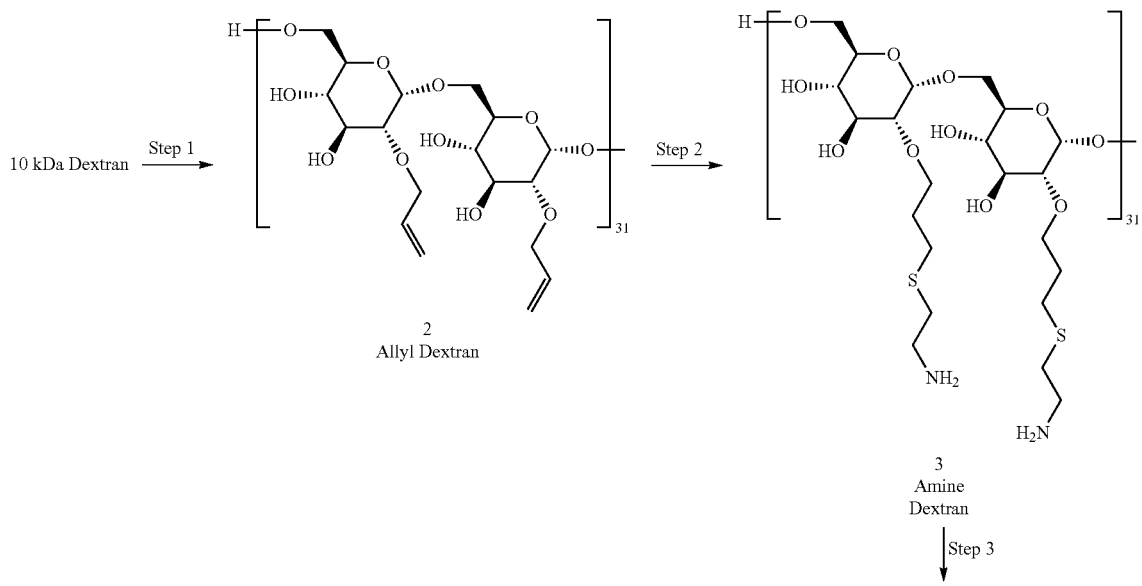

Scheme 1-Stepwise Route and Intermediates for Synthesis of Tilmanocept and the DOTA Derivative

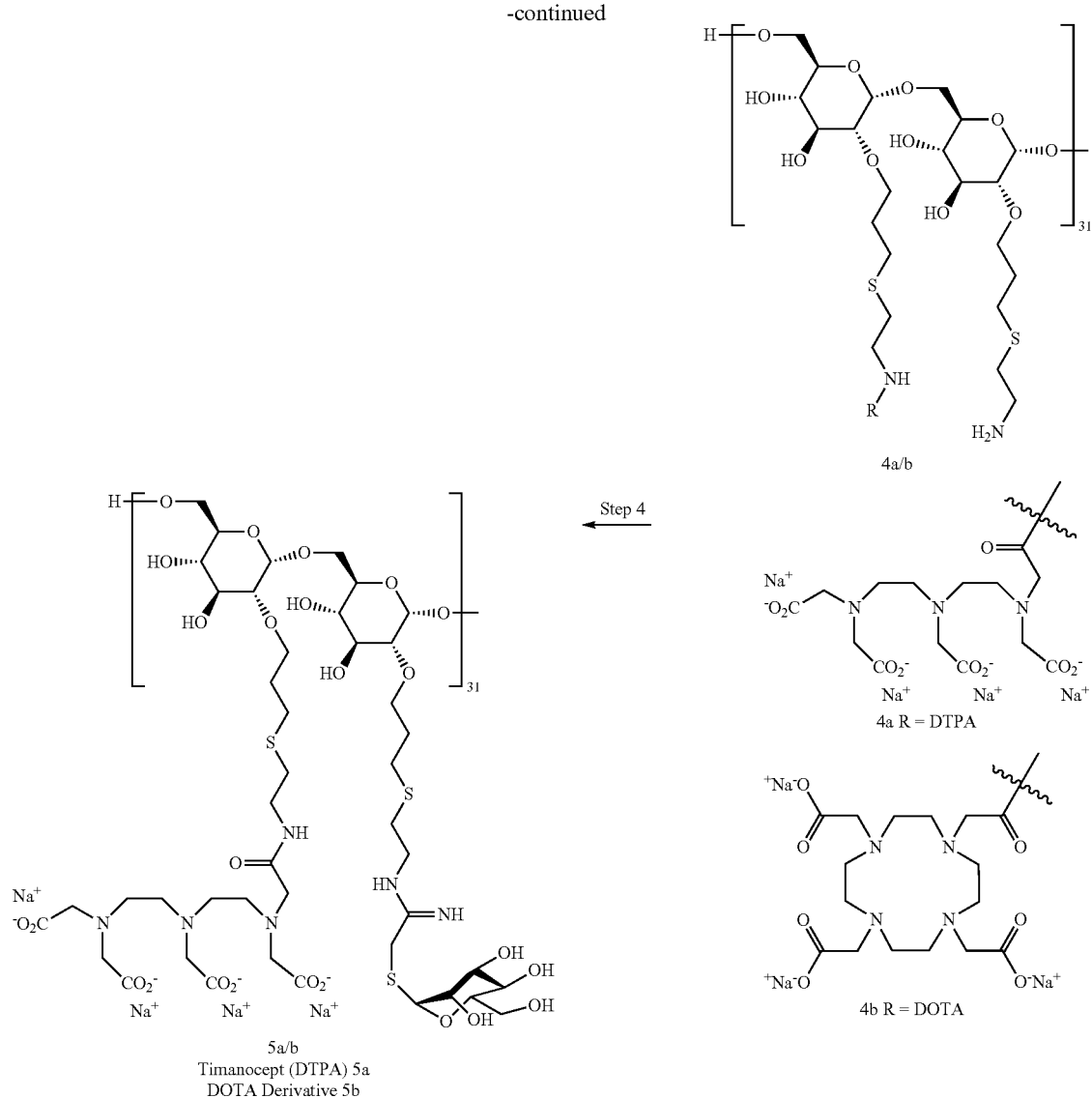

5a/b
Timanocept (DTPA) 5a
DOTA Derivative 5b substances exit the blood flow and penetrate into tissues less efficiently than do smaller molecular weight substances. In addition, substances smaller than 30 kDa tend to be excreted into the urine, while substances greater than 40 kDa tend to be retained in the blood. Thus, crosslinking can alter the biodistribution and pharmacokinetics of a mannosylated dextran such as tilmanocept and adversely affect its ability to localize to aggregations of CD206 expressing cells at site of ongoing pathologies. The utility of tilmanocept and other mannosylated dextrans to address the various envisioned indications involving chelators could be significantly improved if crosslinking during chelator addition could be avoided.

In the process described in the '990 Patent, isobutyl chloroformate (IBCF) is used to derivatize DTPA to prepare it for conjugation to the amine terminated leashes. The '990 Patent teaches that limiting the molar concentration of the activating reagent IBCF relative to that of DTPA eliminates crosslinking during the DTPA conjugation reaction. While it is true that this strategy reduces crosslinking in the DTPA conjugation reaction, it does not eliminate it. Even when IBCF concentrations are reduced by 50%, at least half of the amine dextran molecules become cross-linked during the DTPA conjugation.

CD206 is normally expressed on macrophages, macrophage-like cells (e.g. Kupffer cells of the liver), many dendritic cells, and the mesangial cells of the kidneys. In lesions of many societally important illnesses (e.g. cancer, atherosclerosis, and rheumatoid arthritis among others) large numbers of macrophages can aggregate. In many cases, the pathology associated macrophages express elevated levels of CD206. There are many potential medical indications for which imaging macrophages in and/or delivering non-radioactive metal ions to these lesions could have great clinical utility. Depending on the chelated radioisotope delivered, tilmanocept or related molecular constructs could be imaged by planar gamma imaging, single-photon emission computed tomography (SPECT), or positron emission tomography (PET), with or without concurrent x-ray computed tomography (CT) or other imaging modality. There are also potential medical indications where it would be beneficial to deliver non-radioactive metal ions to CD206 expressing cells. The ability of tilmanocept or related construct to enable imaging macrophages or deliver non-radioactive metal ions to CD206 expressing macrophages in these lesions is compromised when the tilmanocept or related construct is crosslinked or oligomerized causing its average molecular weight and polydispersity to significantly increase. Accordingly, there is a need in the art for an improved process for producing tilmanocept or related constructs that reduces or eliminates crosslinking and/or oligomerization.

BRIEF SUMMARY

Figure 1A:
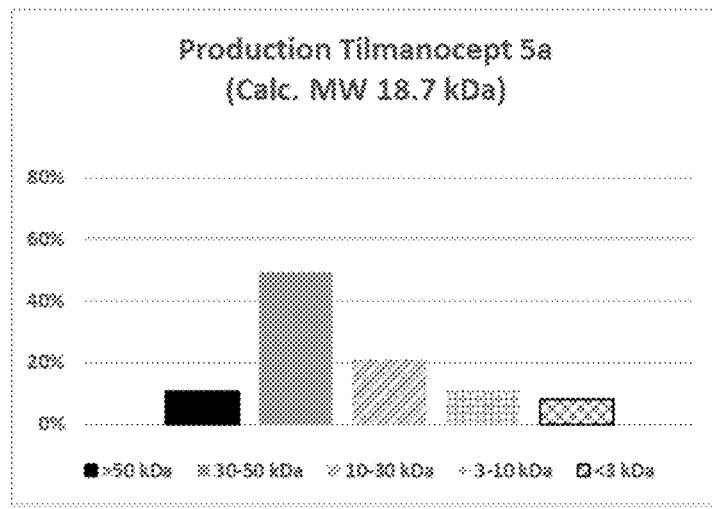
FIG. 1a shows the spin-filter distribution of tilmanocept prepared accruing to the process of Scheme 1.

Disclosed herein is method for conjugating a metal chelating agent to a functionalized dextran by reacting a chelator with an aminated dextran backbone, where the chelator comprises a one, and only one, derivatized carboxylic acid group to form a chelator-dextran complex. In certain aspects, the dextran-chelator complex is substantially free of intra- or intermolecular crosslinking. In certain aspects, the functionalized dextran is an amine dextran, an alkynyl dextran, or a thiol dextran. In exemplary implementations, the functionalized dextran is an amine dextran. In further embodiments, one and only one carboxylic acid group on the chelating agent is derivatized as a N-hydroxysuccinimide (NHS) ester.

According to certain embodiments, the chelator is 1,4,7,10-tetraazacyclododecane-1,4,7,10-tetraacetic acid (DOTA). In certain implementations, the chelator further comprises a plurality of carboxylic acid groups, each conjugated to a protecting group. In certain embodiments of these implementations, the method further includes removing the protecting groups from the chelator-dextran complex. In certain embodiments the protecting groups are chosen from a list consisting of t-butyl esters, benzyl esters, phenyl esters, allyl esters, silyl esters, methyl esters, trifluoromethyl esters, ortho esters, oxazolines, and thioesters. In further embodiments, the protecting groups are t-butyl groups.

According to certain further embodiments, the chelator is diethylenetriaminepentaacetic acid (DTPA).

In certain implementations, prior to reacting the chelator with the aminated dextran backbone, the chelator is synthesized by activating a chelator with a plurality of carboxylic acid groups conjugated to protecting groups and a single active carboxylic acid groups to form a mono-NHS-chelator. In certain embodiments, the protecting groups may be t-butyl esters, benzyl esters, phenyl esters, allyl esters, silyl esters, methyl esters, trifluoromethyl esters and ortho esters, oxazolines, and/or thioesters. In exemplary embodiments of these implementations, each of the plurality of protecting groups is removed, prior to reaction with the dextran backbone. In certain embodiments, the chelator is DTPA.

Further disclosed herein is a method for synthesizing a monomeric a mannosylated dextran (e.g., tilmanocept) by reacting a chelator with an aminated dextran backbone, wherein the chelator comprises a plurality of carboxylic acid groups, each conjugated to a protecting group and a single activated mono-N-hydroxysuccinimide (NHS) ester, to form a chelator-dextran complex;

removing the protecting groups from each of the plurality of carboxylic acid groups; and adding a plurality of mannose moieties to the chelator dextran complex through amidate linkage to the dextran backbone. In certain embodiments, the chelator is DTPA. In certain embodiments, the protecting groups are chosen from a list consisting of: t-butyl esters, benzyl esters, phenyl esters, allyl esters, silyl esters, methyl esters, trifluoromethyl esters ortho esters, oxazolines, and thioesters. In certain embodiments, the protecting groups are t-butyl groups.

Further disclosed herein is a substantially pure monomeric compound comprising a dextran backbone having one or more CD206 targeting moieties and one or more diagnostic moieties attached thereto. In certain implementations, the compound is a compound of Formula (II):

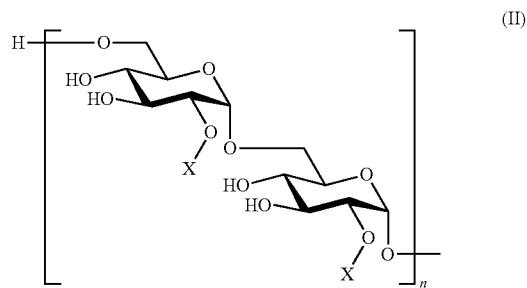

wherein
each X is independently H, L1-A, or L2-R; each L1 and L2 are independently linkers;
each A independently comprises a detection moiety or H;
each R independently comprises a CD206 targeting moiety or H; and
n is an integer greater than zero; and
wherein at least one R is a CD206 targeting moiety and at least one A is a diagnostic moiety or a therapeutic moiety.

In certain embodiments, at least about 60% of the compound is between about 10 and about 30 kDa. In further embodiments, the dextran backbone of the compound is about 3.5 kDa.

DETAILED DESCRIPTION

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH2CH2O— units in the polyester, regardless of whether ethylene glycol was used to prepare the polyester. Similarly, a sebacic acid residue in a polyester refers to one or more —CO(CH2)8CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A1," "A2," "A3," and "A4" are used herein as generic symbols to represent various specific substituents. These symbols can be any substituent, not limited to those disclosed herein, and when they are defined to be certain substituents in one instance, they can, in another instance, be defined as some other substituents.

"R1," "R2," "R3," "Rn," where n is an integer, as used herein can, independently, possess one or more of the groups listed above. For example, if R1 is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

The term "arylalkyl" or "aralkyl" as used herein denotes the radical R'R"—, wherein R' is an aryl radical as defined herein, and R" is an alkylene radical as defined herein with the understanding that the attachment point of the arylalkyl moiety will be on the alkylene radical. Examples of arylalkyl radicals include, but are not limited to, benzyl, phenylethyl and 3-phenylpropyl.

The term "alkoxy group" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "$C_{1-10}$ alkoxy" as used herein refers to an-O-alkyl wherein alkyl is $C_{1-10}$.

The term "alkylene" as used herein denotes a divalent linear or branched saturated hydrocarbon radical, having from four to six carbons inclusive, unless otherwise indicated. Examples of alkylene radicals include propylene, butylene, pentylene or hexylene.

The term "cycloalkyl" as used herein denotes a saturated carbocyclic ring containing 3 to 7 carbon atoms, i.e. cyclopropyl, cyclobutyl, cyclopentyl, cyclohexyl or cycloheptyl. "$C_{3-7}$ cycloalkyl" as used herein refers to an cycloalkyl composed of 3 to 7 carbons in the carbocyclic ring.

The term "alkanol" as used herein means an HO-alkyl group, wherein alkyl is as defined above such as methanol, ethanol, n-propanol, i-propanol, n-butanol, i-butanol, t-butanol, including their isomers.

The term "urethane" as used herein refers to a group ROC(=O)NH— where the nitrogen atom is an alpha-amino group of an amino acid. R in the urethane is alkyl as used herein preferably tert-butyl (boc) or R is benzyl (cbz). An equivalent definition for "urethane" as used herein is an alkoxycarbonyl or benzyloxycarbonyl linked to an amino group.

The term "orthoester" as used herein refers to a group RC(OR')3 wherein R is alkyl or hydrogen and R' is alkyl.

The term "aprotic (or nonpolar) solvent" means organic solvents such as diethyl ether, ligroin, pentane, hexane, cyclohexane, heptane, octane, benzene, toluene, dioxane, tetrahydrofuran, carbon tetrachloride.

The term "derivative" of a compound as used herein means a compound obtainable from the original compound by a simple chemical process.

The term "acylating agent" as used herein refers to either an anhydride, acid halide or an activated derivative of an N-protected alpha amino acid. The term "anhydride" as used herein refers to compounds of the general structure RC(O)—O—C(O)R wherein R is an N-protected alpha amino. The term "acid halide" as used herein refers to compounds of the general structure RC(O)X wherein X is a halogen As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

As used herein, "protecting group" refers to a moiety attached to a functional group to prevent an otherwise unwanted reaction of that functional group.

As used herein, the term "pharmaceutically acceptable carrier" or "carrier" refers to sterile aqueous or nonaqueous solutions, colloids, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "subject" refers to the target of administration, e.g., an animal. Thus the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more cancer disorders prior to the administering step.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of crosslinking" would either completely lack crosslinking, or so nearly completely lack crosslinking that the effect would be the same as if it completely lacked crosslinking. In other words, a composition that is "substantially free" of an ingredient or element may still actually contain such item as long as there is no measurable effect thereof.

"Tilmanocept" refers to a non-radiolabeled active pharmaceutical ingredient (API) of the LYMPHOSEEK® diagnostic agent. Tilmanocept is a mannosylaminodextran, a subset of mannosylated dextrans. It has a dextran backbone to which a plurality of amino-terminated leashes (—O (CH$_2$)$_3$ S(CH$_2$)$_2$NH$_2$) are attached to the core glucose hydroxyl elements. In addition, mannose moieties are conjugated to amino groups of a number of the leashes, and the chelator diethylenetriamine pentaacetic acid (DTPA) may be conjugated to the amino group of other leashes not containing the mannose. Tilmanocept generally, has a dextran backbone, in which a plurality of the glucose residues comprise an amino-terminated leash:

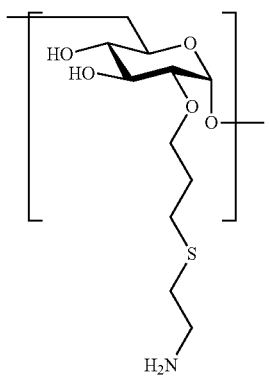

the mannose moieties are conjugated to the amino groups of the leash via an amidine linker:

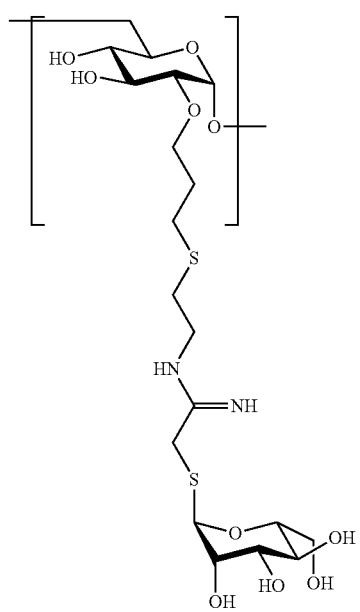

the chelator diethylenetriamine pentaacetic acid (DTPA) is conjugated to the amino groups of the leash via an amide linker:

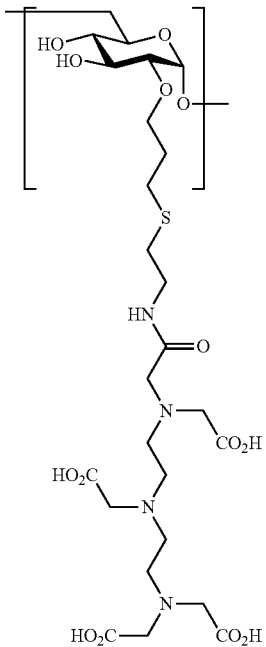

Tilmanocept has the chemical name dextran 3-[(2-aminoethyl)thio]propyl 17-carboxy-10,13,16-tris(carboxymethyl)-8-oxo-4-thia-7,10,13,16-tetraazaheptadec-1-yl 3-[[2-[[1-imino-2-(D-mannopyranosylthio)ethyl]amino]ethyl] thio]propyl ether complexes, and tilmanocept Tc99m has the following molecular formula: [C$_6$H$_{10}$O$_5$]$_n$·(C$_{19}$H$_{28}$N$_4$O$_9$S$^{99m}$Tc)$_b$·(C$_{13}$H$_{24}$N$_2$O$_5$S$_2$)$_c$·(C$_5$H$_{11}$NS)$_a$ and contains 3-8 conjugated DTPA molecules (b); 12-20 conjugated mannose molecules (c); and 0-17 amine side chains (a) remaining free. Tilmanocept has the following general structure:

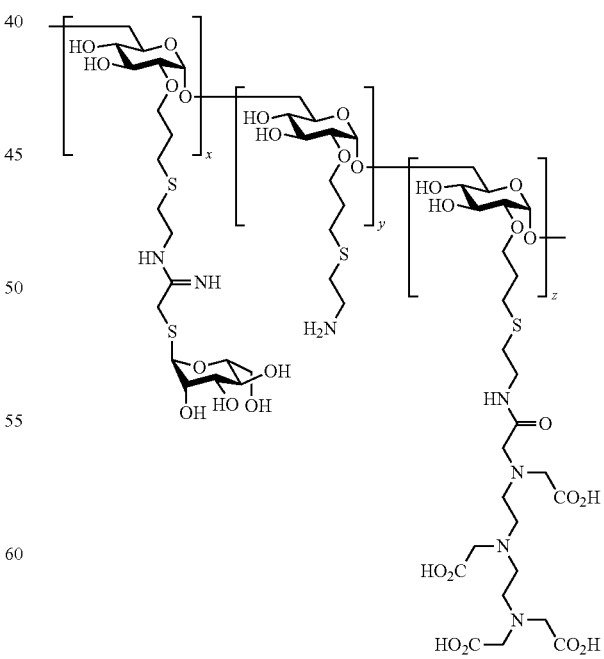

Certain of the glucose moieties may have no attached amino-terminated leash.

When the molecular weight of tilmanocept increases, it penetrates less efficiently into target tissues and lesions causing less of the injected dose to be available to localize to CD206 expressing macrophages. This is expected to reduce the radiographic signal that can be detected by imaging studies. Also, because high molecular weight material is excreted less efficiently into the urine, more of the injected dose is retained in circulation causing the blood pool background signal to increase. The expected result is a decreased signal to noise ratio that would limit imaging sensitivity and accuracy. In addition, because there are limited barriers between the Kupffer and mesangial cells to circulating blood coupled with reduced rates of excretion, more of the injected dose would localize to the liver and kidneys. This off-target exposure to radiopharmaceutical may further reduce the sensitivity of imaging the desired tissues due to shine through effects from the liver and kidney. The same issues would arise if non-radioactive metal ions were being targeted to CD206 expressing lesional macrophages. To remedy all of these deficiencies, what is desired is a synthesis procedure for tilmanocept and related constructs that prevents crosslinking and oligomerization. Such a procedure would create uniformly (or near uniformly) monomeric products without the high molecular weight oligomerized forms.

This disclosure describes new chemical reagents and a modified synthesis protocol that enable the conjugation of chelators (i.e. DTPA and DOTA) to the amine dextran precursor of tilmanocept and related mannosylated dextran molecular constructs that nearly or completely eliminates crosslinking. There are no molecular differences between tilmanocept created by the instantly disclosed processes and the method described in the '990 Patent except that the products prepared by the new method are not crosslinked. The novelty of the products described in this disclosure is that the products so formed are not crosslinked and thus more uniform in molecular weight profile. The utility of this method is that the tilmanocept and other constructs synthesized by the disclosed methods will have improved biodistributions and pharmacokinetic attributes, thus enhanced performance characteristics.

Disclosed herein is a method for conjugating a metal chelating agent to a functionalized dextran by reacting a chelator with a functionalized dextran backbone, wherein the chelator comprises one and only one derivatized carboxylic acid group, to form a chelator-dextran complex that is substantially free of intra- or intermolecular crosslinking. In certain aspects, the functionalized dextran is an amine dextran, an alkynyl dextran, or a thiol dextran. In exemplary implementations, the functionalized dextran is an amine dextran. According to certain implementations of this embodiment the one and only one derivatized carboxylic acid group is a mono-N-hydroxysuccinimide (NHS) ester.

In certain embodiments, the chelator is 1,4,7,10-tetraazacyclododecane-1,4,7,10-tetraacetic acid (DOTA). In certain implementations of these embodiments, the chelator further comprises a plurality of carboxylic acid groups, each conjugated to a protecting group. According to certain embodiments, the protecting groups are t-butyl esters. Other commonly employed carboxylic acid protecting groups (e.g., benzyl esters, phenyl esters, allyl esters, silyl esters, methyl esters, trifluoromethyl esters and ortho esters, oxazolines, thioesters) may be utilized. In certain aspects, the method further comprises removing the protecting groups from the chelator-dextran complex.

According to certain further embodiments, the chelator is diethylenetriaminepentaacetic acid (DTPA).

In certain implementations, various combinations of functionalized dextrans, mono-derivativitized chelators, and protecting groups are possible. These combinations include but are not limited to those shown in the following schemes:

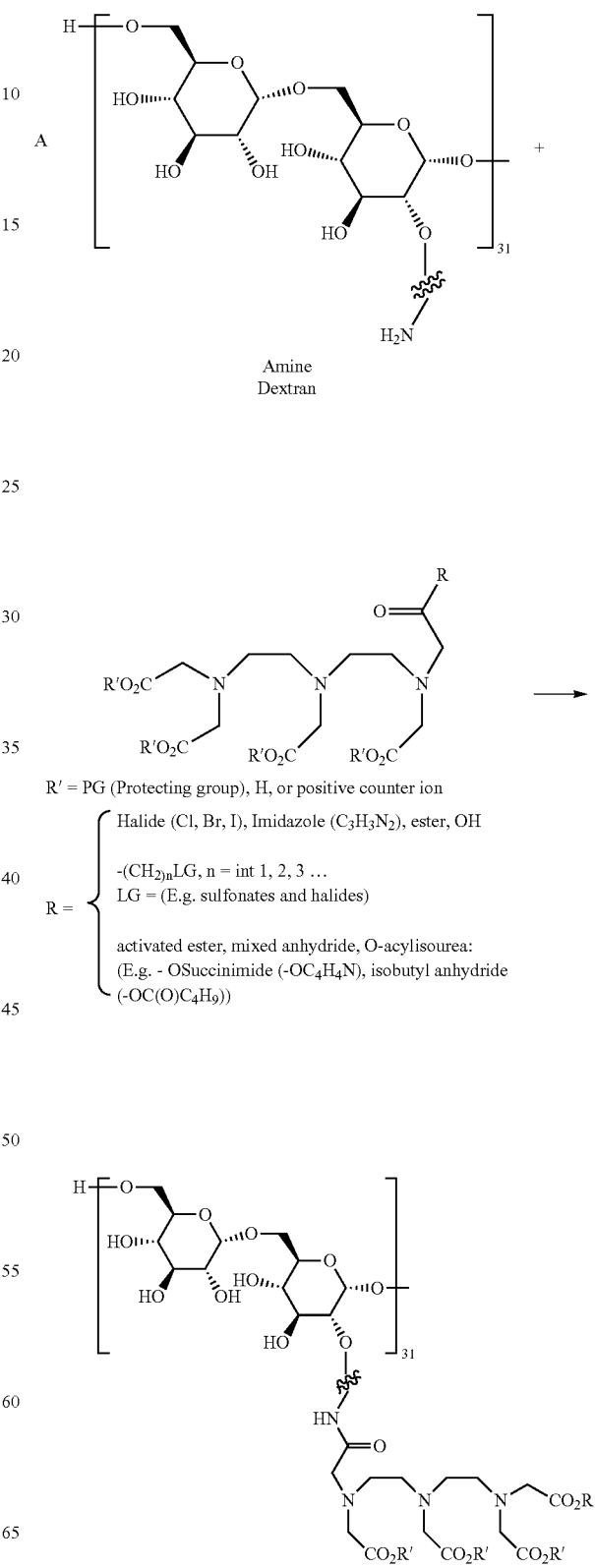

-continued

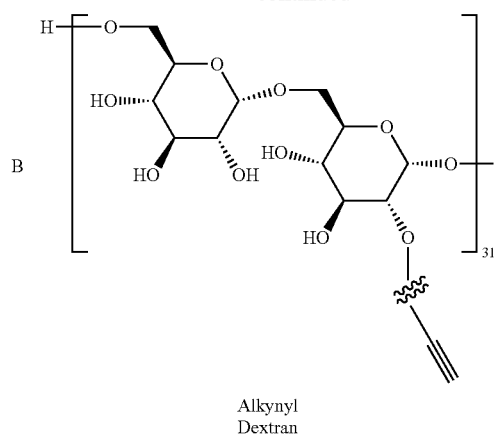

Alkynyl Dextran

-continued

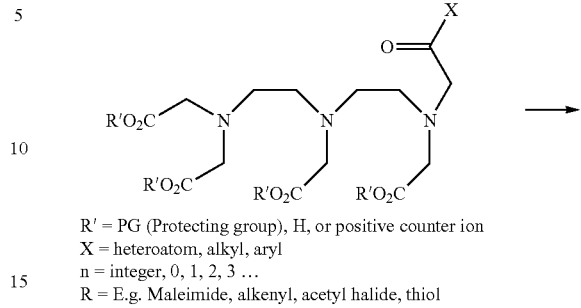

R' = PG (Protecting group), H, or positive counter ion
X = heteroatom, alkyl, aryl
n = integer, 0, 1, 2, 3 ...
R = E.g. Maleimide, alkenyl, acetyl halide, thiol

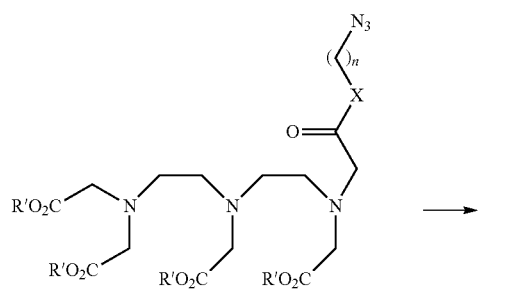

R' = PG (Protection group), H, or positive counter ion
X = heteroatom, alkyl, aryl
n = integer, 0, 1, 2, 3 ...

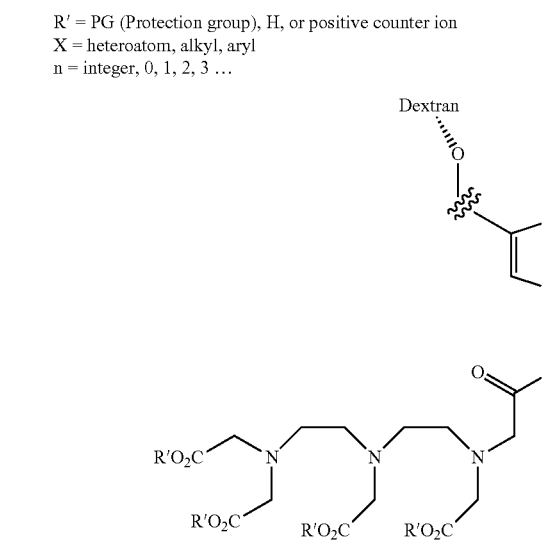

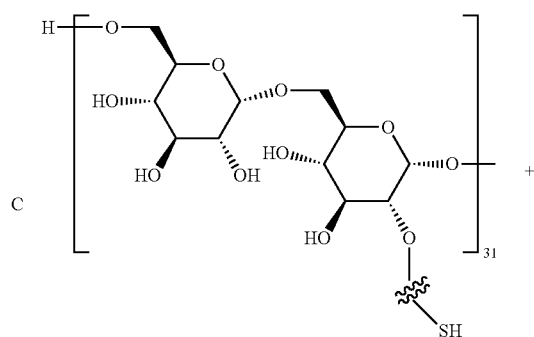

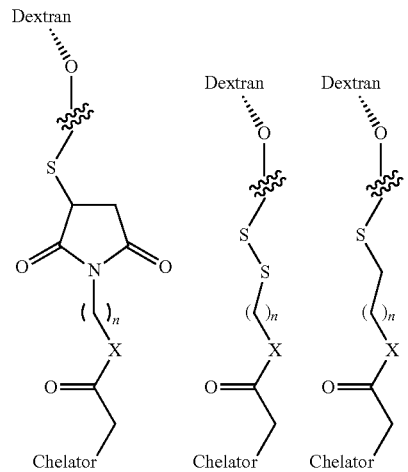

In certain implementations, prior to reacting the chelator with a functionalized dextran backbone, the chelator with a plurality of carboxylic acid groups conjugated to protecting groups and a single free carboxylic acid group is functionalized to form a mono-activated chelator (e.g. one and only one of the plurality of carboxylic acid groups is activated for attachment to the dextran backbone). In exemplary aspects, the mono-activated chelator is a mono-NHS-chelator. In certain exemplary implementations, each of the plurality of protecting groups is removed, prior to reaction with the dextran backbone.

Further disclosed herein is a method for synthesizing a monomeric tilmanocept by reacting a chelator with an aminated dextran backbone, wherein the chelator comprises a plurality of carboxylic acid groups, each conjugated to a protecting group and a single activated mono-N-hydroxysuccinimide (NHS) ester, to form a chelator-dextran complex; the protecting groups from each of the plurality of carboxylic acid groups; and adding a plurality of mannose moieties to the chelator dextran complex through amidate linkage to the dextran backbone. In exemplary implementations, the chelator is DTPA. In further implementations, the protecting groups are t-butyl groups.

Further disclosed herein is a substantially pure monomeric compound comprising a compound of Formula (I):

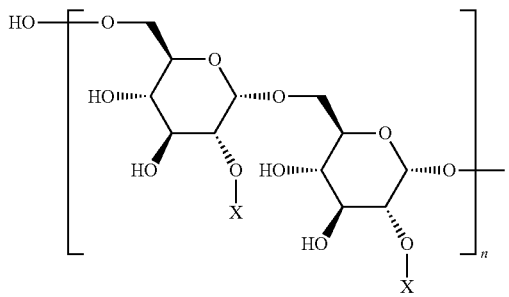

wherein
each X is independently H, L1-A, or L2-R;
each L1 and L2 are independently linkers;
each A independently comprises a therapeutic agent or a detection moiety or H;
each R independently comprises a mannose-binding C-type lectin receptor targeting moiety or H;
and n is an integer greater than zero; and
wherein at least one R comprises a mannose-binding C-type lectin receptor targeting moiety selected from the group consisting of mannose, fucose, and N-acetylglucosamine and at least one A comprises a therapeutic agent.

Further disclosed herein is a substantially pure monomeric compound comprising a dextran backbone having one or more CD206 targeting moieties and one or more diagnostic moieties or therapeutic moiety attached thereto.

In certain aspects, the compound is a compound of Formula (II):

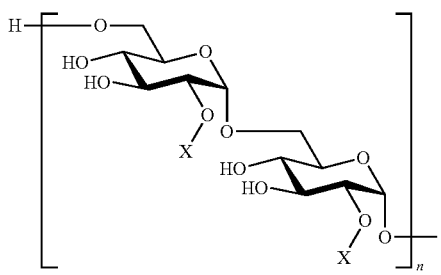

wherein
each X is independently H, L1-A, or L2-R; each L1 and L2 are independently linkers;
each A independently comprises a detection moiety or H; each R independently comprises a CD206 targeting moiety or H; and n is an integer greater than zero; and wherein at least one R is a CD206 targeting moiety and at least one A is a diagnostic moiety or therapeutic moiety.

In certain aspects, the at least one A is a gamma-emitting agent. In further aspects, at least one A is a PET agent. In yet further aspects, at least one A is an isotope. In exemplary implementations, the at least one A is selected from the group consisting $^{99m}$Tc, $^{210}$Bi, $^{212}$Bi, $^{213}$Bi, $^{214}$Bi, $^{131}$Ba, $^{140}$Ba, $^{11}$C, $^{14}$C, $^{51}$Cr, $^{67}$Ga, $^{68}$Ga, $^{153}$Gd, $^{88}$Y, $^{90}$Y, $^{91}$Y, $^{123}$I, $^{124}$I, $^{125}$I, $^{131}$I, $^{111}$In, $^{115m}$In, $^{18}$F, $^{13}$N, $^{105}$Rh, $^{153}$Sm, $^{67}$Cu, $^{64}$Cu, $^{166}$Ho, $^{177}$Lu, $^{223}$Ra, $^{62}$Rb, $^{186}$Re and $^{188}$Re, $^{32}$P, $^{33}$P, $^{46}$Sc, $^{47}$Sc, $^{72}$Se, $^{75}$Se, $^{35}$S, $^{89}$Sr, $^{182}$Ta, $^{123}$mTe, $^{127}$Te, $^{129}$Te, $^{132}$Te, $^{65}$Zn and $^{89}$Zr, $^{95}$Zr.

In certain embodiments, at least about 60% of the disclosed compound is between about 10 and about 30 kDa. In certain implementations, constructs will have an Mw of about 7 kDa and will have the majority of their masses between 5-10 kDa. In certain implementations, the dextran backbone is about 5 kDa.

There are many potential medical indications besides SLN identification for which mannosylated dextrans conjugated with chelators may provide clinical utility. These alternative indications encompass any disease state in which CD206 expressing cells aggregate. Examples of such indications include, but are not limited to, cancer, atherosclerosis, rheumatoid arthritis and many others. Depending on the specific indication, the metal ions chelated to the mannosylated dextran constructs may be either radioactive or not. Examples of potential radioactive metal ions that could be chelated to treat these various metal medical indications include, but are not limited to, $^{99m}$Tc, $^{210}$Bi, $^{212}$Bi, $^{213}$Bi, $^{214}$Bi, $^{131}$Ba, $^{140}$Ba, $^{11}$C, $^{14}$C, $^{51}$Cr, $^{67}$Ga, $^{68}$Ga, $^{153}$Gd, $^{88}$Y, $^{90}$Y, $^{91}$Y, $^{123}$I, $^{124}$I, $^{125}$I, $^{131}$I, $^{111}$In, $^{115m}$In, $^{18}$F, $^{13}$N, $^{105}$Rh, $^{153}$Sm, $^{67}$Cu, $^{64}$Cu, $^{166}$Ho, $^{177}$Lu, $^{223}$Ra, $^{62}$Rb, $^{186}$Re $^{188}$Re, $^{32}$P, $^{33}$P, $^{46}$Sc, $^{47}$Sc, $^{72}$Se, $^{75}$Se, $^{35}$S, $^{89}$Sr, $^{182}$Ta, $^{123}$mTe, $^{127}$Te, $^{129}$Te, $^{132}$Te, $^{65}$Zn and $^{89}$Zr, $^{95}$Zr. Examples of nonradioactive metal ions that may be enable various medical indications include, but are not limited to stable isotopes of Fe, Cu, Ag, Cr, Zn, Cd, Ni, Mo, Mn, As, Sb, Bi, Ga, In, Pd, Ru and OS. Also, depending on the specific medical indication being addressed, the preferred size of the dextran backbone on which the mannosylated dextran construct is synthesized may vary from 1.0 kDa to 500 kDa. Finally, for some medical indications, a chelator other than DTPA may be preferred. A common example of an alternative chelator that may be used is 1,4,7,10-Tetraazacyclododecane-1,4,7,10-tetraacetic acid (DOTA).

The current disclosure describes improved synthesis pathways that avoid crosslinking for conjugating DTPA and DOTA to mannosylated dextrans. The same synthesis strategy disclosed herein may have utility for conjugating a wide variety of other chelators to mannosylated dextrans while avoiding crosslinking. Our studies have shown that the activation and addition of unprotected metal-chelators such as DTPA to amine dextran is largely responsible for the generation of these polymeric species and the molecular weight variability observed in tilmanocept batches (Step 3, Scheme 1). While strategies are available to limit the crosslinking of the amine chains on dextran, the current tilmanocept synthesis protocol for activating one of the five free carboxylic acid moieties on a given chelator is problematic, resulting in multiply activated sites. Multiply activated chelators (e.g. DTPA) can react with multiple amine groups on the amine dextran, tilmanocept precursor (Step 3 in Scheme 1) resulting in intra- and intermolecular crosslinking as shown in Scheme 2. This reaction between multiply activated chelators and the amine dextran is the most significant if not the sole source of oligomerization of tilmanocept observed in the products of the current synthesis protocol. In contrast, appending a metal-binding agent bearing a single, activated acid would ameliorate the oligomerization of amine dextran, producing a polymer product of desired Mw profile and with polydispersity comparable to the starting dextran (i.e. PDI 1.3-1.4).

DTPA is not the only chelator that can be conjugated to amine dextrans to create imaging and therapeutic agents capable of delivering radioactive and non-radioactive metal ions to specific targets such as CD206 expressing cells. For some indications, other chelators, such as DOTA (1,4,7,10-Tetraazacyclododecane-1,4,7,10-tetraacetic acid, 4b in Scheme 1) may be preferred. Furthermore, the molecular weight of the starting dextran backbone can be modified. For example, starting dextran backbones with Mw of about 3.5 kDa, 5 kDa, 10 kDa, 20 kDa, 40 kDa or larger may be preferred for various indications. In addition, the final constructs can be targeted to various receptors by replacing some or all of the mannose moieties on tilmanocept with other targeting moieties. Examples of other targeting moieties could include but are not limited to other sugars (e.g. galactose), peptides, nucleic acids, and ligands for somatostatin receptors (SSR). The current invention describes a synthesis strategy and compositions of matter for conjugating chelators to amine dextrans without undesirable cross-linking. Other attributes of the final molecular construct are possible.

EXAMPLES

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and

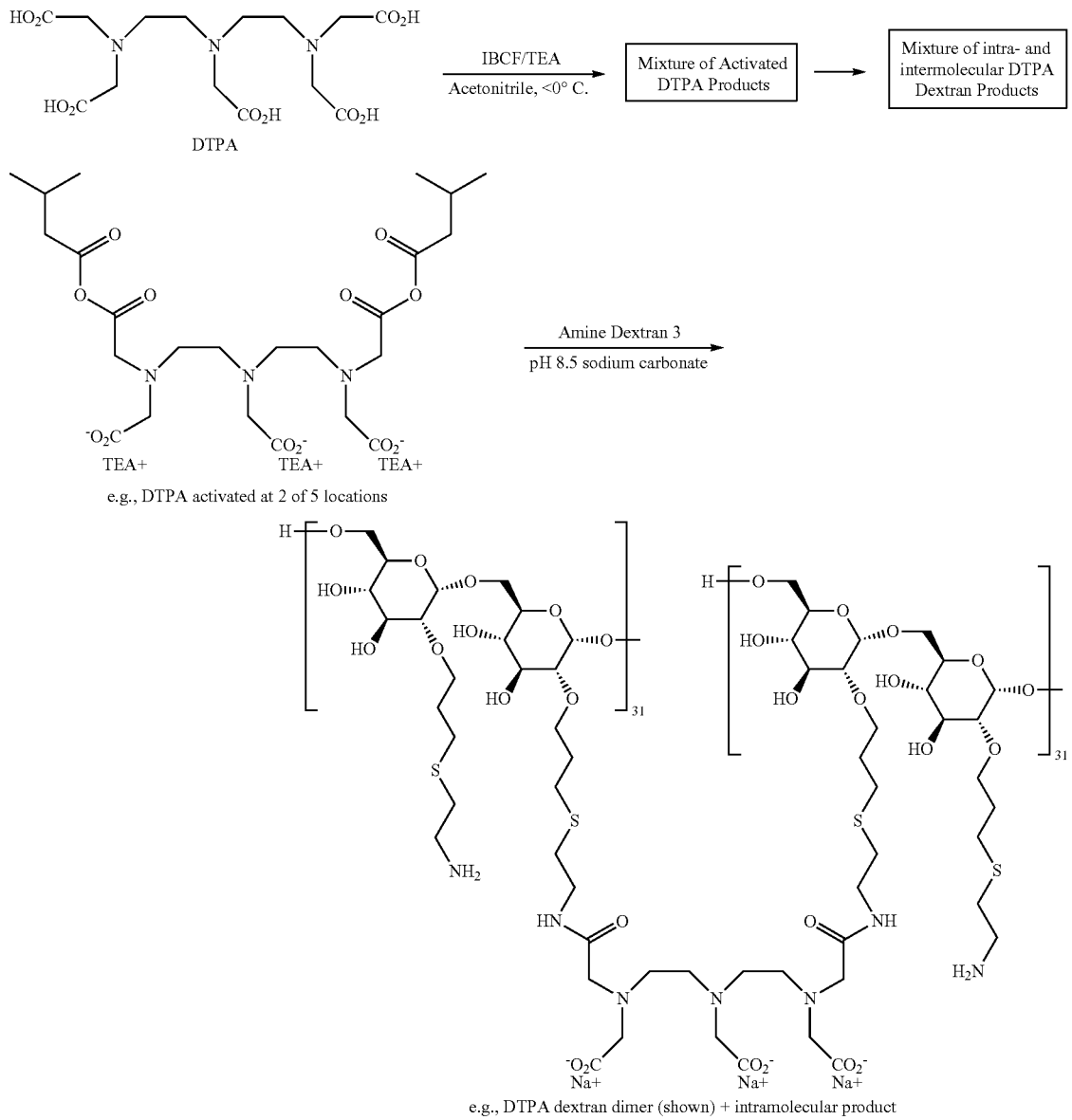

still obtain a like or similar result without departing from the spirit and scope of the invention.

What follows are the first examples describing a novel synthesis strategy for conjugating chelators to amine dextrans without undesired crosslinking. The Examples describe the conjugation of DTPA and DOTA to amine dextrans and have immediate utility for improving synthesis of tilmanocept and related products by enabling the creation of final synthesis products that are predominately monomeric and not oligomerized or crosslinked.

Example 1: Uniformly Defined Molecular Weight DTPA and Mannose Derivatized 10 kDa Dextran, (Tilmanocept)

During the manufacture of tilmanocept, DTPA is activated as a mixed anhydride using isobutylchloroformate (IBCF) at low temperature for condensation with amino groups on amine dextran (Scheme 1). There are 5 carboxylic acid groups on a DTPA molecule, which can react independently with IBCF to become activated. Thus, any number or all (0-5) of these carboxylic acid groups may become activated during this activation process. When two or more carboxylic acid groups become activated, crosslinking as shown in Scheme 2 is possible, resulting in a range of oligomeric species of increased molecular weight. Intramolecular croslinking can also occur, which may negatively impact the ability of the molecule to bind avidly to CD206. While varying the molar ratio of IBCF to DTPA in the reaction can alter the portion of DTPA molecules with two or more activated carboxylic acid groups, it is important to note that there is no molar ratio of IBCF to DTPA that does not result in a portion of the DTPA molecules being activated at two or more sites. This is the deficiency of the previous approaches, such as that described in the '990 Patent, that is remedied by the current invention.

The starting amine-dextran 3 in this reaction is generated in two steps from commercially available 10 kDa dextran and has been previously described (Scheme 1), involving the allylation of dextran with PDI≤1.4 in aqueous sodium hydroxide (Step 1, Scheme 1) followed by radical addition of 2-aminoethanethiol (Step 2, Scheme 1). The chemical composition and molar ratios of the reagents utilized to produce amine-dextran 3 are the same regardless of the size of the starting dextran polymer. On average, 40-60% of the glucose units in this material bears an amine-terminated chain (25-37 per 10 kDa dextran) and the overall PDI is approximately equal to the starting dextran.

In certain embodiments, a single carboxylic acid group on DTPA is activated as the mono-N-hydroxysuccinimide (NHS) ester prepared from commercially available diethylenetriamine-N,N,N"-tetra-tert-butyl acetate-N'-acetic acid (DTPA-Tetra, CAS [174267-71-1], Scheme 3) and adapted from a protocol for synthesis of the mono-NHS ester of DOTA. In this way, four of the five acid groups are protected as t-butyl esters, leaving one free carboxylic acid available for activation and addition to amine dextran. The transformation to NHS ester is readily achieved using numerous common protocols, solvents and reagents. However, activation in dry dichloromethane with a slight excess of NHS, triethylamine (TEA) and N,N'-dicyclohexylcarbodiimide (DCC) at room temperature provides the desired product with minimal effort, only requiring filtration of the urea by-product and concentration in vacuo.

The fully-protected mono-NHS DTPA 6 may be directly added to the dextran backbone forming 4' followed by removal of the t-butyl protecting groups (Route A, Scheme 3), or deprotected and added to amine dextran 3 as the tetra free acid 7 (Route B, Scheme 3). In route A, the protected DTPA mono-NHS ester 6 (0.5 M in DMF) is added portion wise to a 3:2 0.1 M sodium bicarbonate-carbonate pH 8.6 buffer/DMF solution of amine dextran 3. Reaction progress is determined by monitoring changes in the amine concentration. At the desired loading of DTPA to the backbone (ave. 3-8 per 10 kDa dextran chain), the material is isolated by UF concentration using a 3 kD molecular weight cut-off (MWCO) membrane and lyophilized. The t-butyl protecting groups of the dextran-bound DTPAs are subsequently removed in DMSO-TFA or 85% phosphoric acid solution followed by neutralization, UF concentration and lyophilization. Although this is a feasible route to DTPA dextran 4a, it is advisable to avoid exposure of the dextran to the highly acidic conditions utilized for removal of the t-butyl groups on 4'.

In route B, addition of the mono-NHS tetra acid 7 to amine dextran requires t-butyl deprotection of 6 as a first step in anhydrous DCM/TFA, concentration and precipitation from methanol/diethyl Scheme 3- Addition of mono-NHS DTPA to Amine Dextran 3

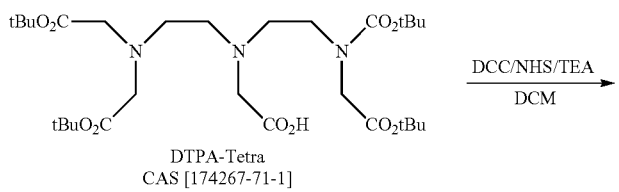

DTPA-Tetra
CAS [174267-71-1]

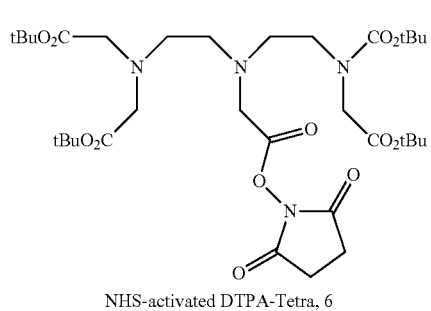

NHS-activated DTPA-Tetra, 6

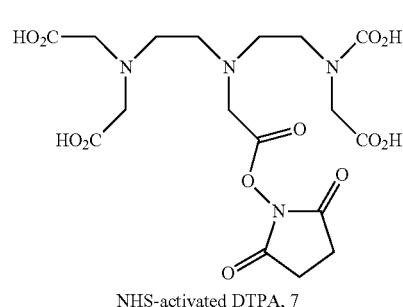

NHS-activated DTPA, 7

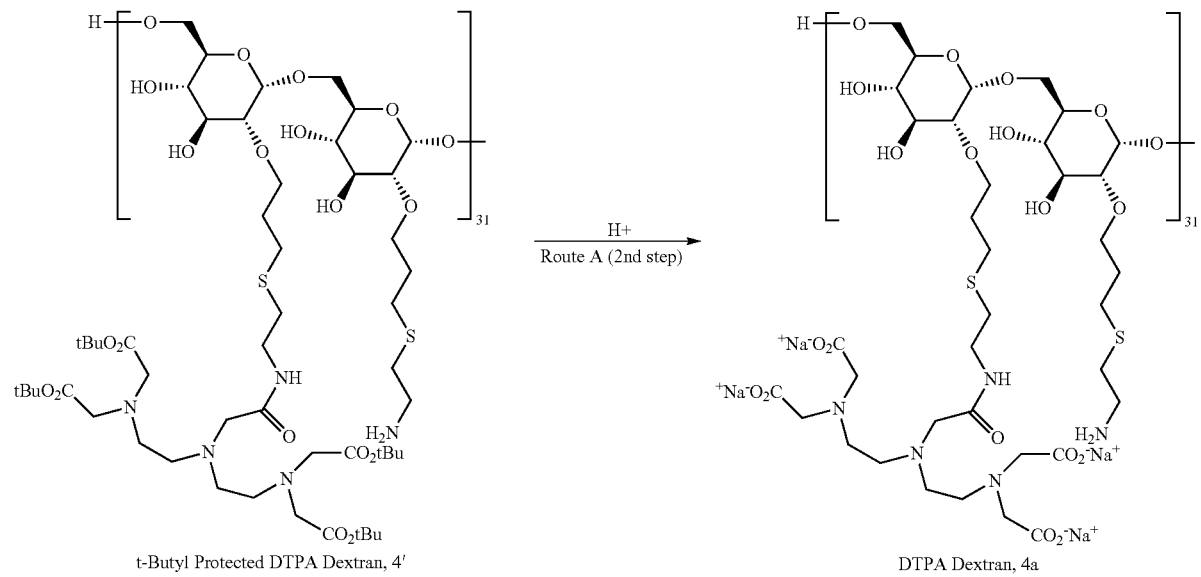

ether. The resulting off-white product is added as a solid to a 0.1 M sodium bicarbonate-carbonate pH 8.6 buffer solution of amine dextran 3 and isolated as described above.

In route B, addition of the mono-NHS tetra acid 7 to amine dextran requires t-butyl deprotection of 6 as a first step in anhydrous DCM/TFA, concentration and precipitation from methanol/diethyl ether. The resulting off-white product is added as a solid to a 0.1 M sodium bicarbonate-carbonate pH 8.6 buffer solution of amine dextran 3 and isolated as described above.

Preparation of mono-NHS DTPA 7: 150 mg (0.24 mmol) of diethylenetriamine-N,N,N,N''-tetra-tert-butyl acetate-N'-acetic acid (DTPA-Tetra, CAS [174267-71-1]) is charged as a powder into a dry flask and dissolved in 6.9 ml of anhydrous dichloromethane under inert atmosphere. 31 mg (0.27 mmol, 1.1 equivalent) of N-hydroxysuccinimide is added to the flask followed by 55 mg (0.27 mmol, 1.1 equivalent) of N,N'-dicyclohexylcarbodiimide and 74 ul (0.53 mmol, 2.2 equivalents) of triethylamine. The solution is stirred at room temperature under inert atmosphere for 15-20 hours. The insoluble dicyclohexylurea by-product is filtered from the mixture and the clear filtrate solution cooled on an ice-bath. 2 volumes of dry TFA is slowly added to the chilled NHS-activated DTPA-Tetra 6 solution and stirring continued under inert gas for 4 hours. The solvents are removed via vacuum concentration at room temperature followed by drying on hi-vacuum for 15 hours resulting in crude 7 as a glassine solid. After dissolving briefly in methanol, 7 is isolated as an off-white powder after filtration by precipitation with diethyl ether.

Preparation of DTPA Dextran 4a: 150 mg of amine dextran 3 is solubilized in 0.1M sodium carbonate-bicarbonate pH 8.6 buffer at 25 mg/ml using brief sonication and stirring at ambient temperature for 30 minutes. A sample of the starting dextran solution is removed as a reference of reaction progress. Solid mono-NHS DTPA 7 is charged to the amine dextran solution in portions while frequently monitoring the change in amine content versus the starting solution by fluorescamine assay (CAS [38183-12-9]). Using an ethanolamine standard curve, the approximate DTPA loading is determined by the percentage of remaining amine and the known average number of amine-terminated chains on the starting dextran. When the desired DTPA loading is achieved (typically 3-8), the reaction is concentrated with 0.1M aqueous sodium carbonate via 3 kDa MWCO ultra-filtration to remove free DTPA followed by concentration with purified water until the filtrate runs a neutral pH. The retentate product solution is frozen and lyophilized providing an off-white foam. The total DTPA in 4a is determined by spectrophotometric iron-chelation assay at 380 nm and free (unbound) DTPA by HPLC. 151 mg, 4.9 DTPA per dextran chain.

Example 2: Uniformly Defined Molecular Weight DOTA and Mannose Derivatized 3.5 and 10 kDa Dextrans The synthesis of the DOTA mimetic of dextrans, functionalized with DOTA rather than DTPA diverges from tilmanocept at the point of appending the metal-chelating agent via an amide bond to an amine-dextran backbone (Scheme 4). 1,4,7,10-Tetraazacyclododecane-1,4,7,10-tetraacetic acid mono-N-hydroxysuccinimide ester, DOTA-NHS, CAS [170908-81-3], the commercially available fully deprotected mono-NHS ester of DOTA is added as a solid to a 0.1 M sodium bicarbonate-carbonate pH 8.6 buffer solution of amine dextran. Reaction progress is determined by changes in amine concentration. At the desired loading of DOTA to the backbone the material is isolated by UF concentration using a 3 kD MWCO membrane and lyophilized.

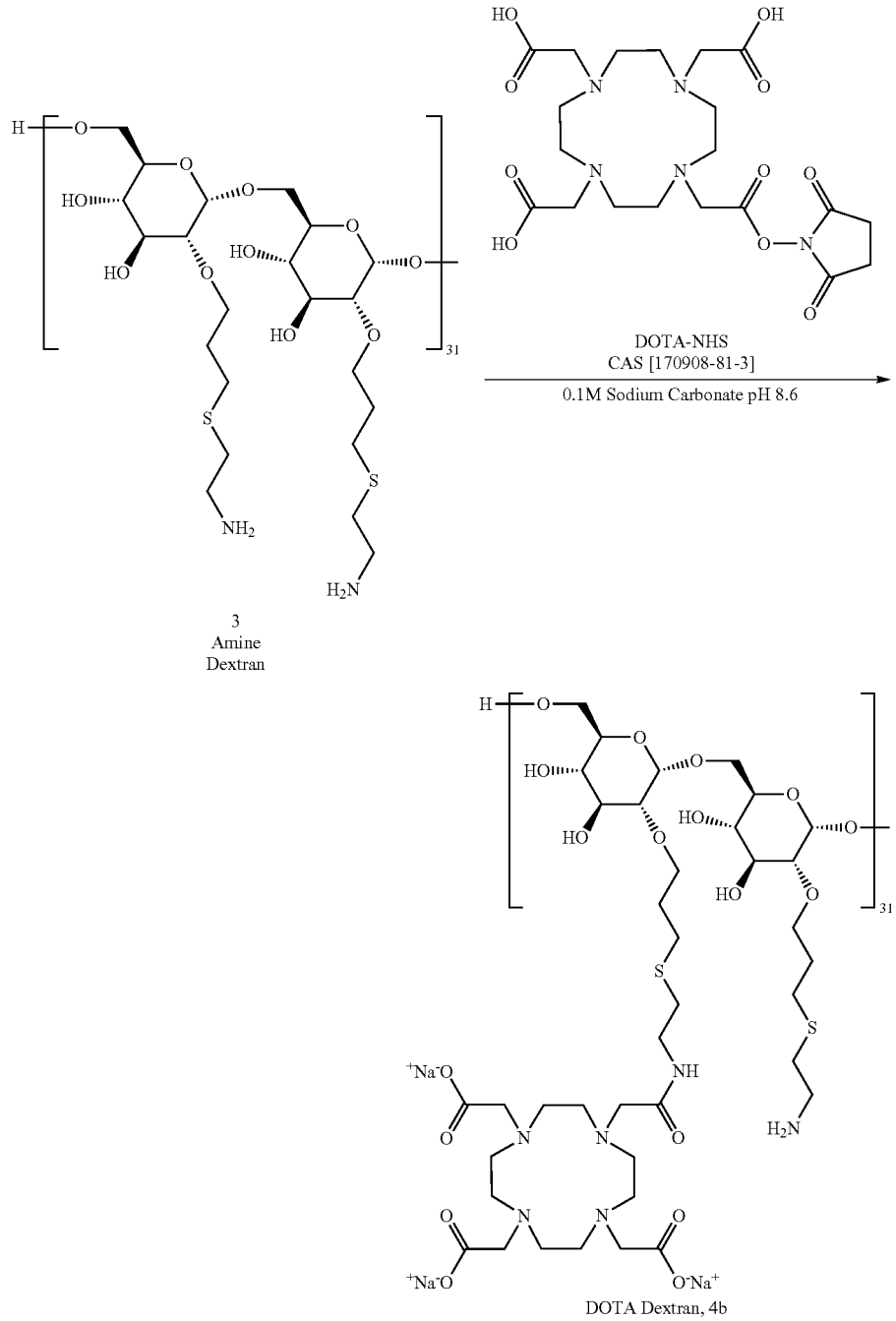

Scheme 4- Addition of mono-NHS DOTA to Amine Dextran 3

Preparation of DOTA Dextran 4b on 10 kDa dextran backbone: 150 mg of amine dextran 3 is solubilized in 0.1M sodium carbonate-bicarbonate pH 8.6 buffer at 25 mg/ml using brief sonication and stirring at ambient temperature for 30 minutes. A sample of the starting dextran solution is removed as a reference of reaction progress. Solid DOTA-NHS is charged to the amine dextran solution in portions while frequently monitoring the change in amine content versus the starting solution by fluorescamine assay (CAS [38183-12-9]). Using an ethanolamine standard curve, the approximate DOTA loading is determined by the percentage of remaining amine and the known average number of amine-terminated chains on the starting dextran. When the target DOTA loading is achieved (typically 3-8), the reaction is concentrated with 0.1M aqueous sodium carbonate via 3 kDa MWCO ultrafiltration to remove free DOTA followed by concentration with purified water until the filtrate runs a neutral pH. The retentate product solution is frozen and lyophilized providing an off-white foam. The total DOTA in 4b is determined by spectrophotometric iron-chelation assay at 380 nm and free (unbound) DOTA by HPLC. 153 mg, 7.0 DOTA per dextran chain.

Preparation of DOTA Dextran 4b on 3.5 kDa dextran backbone: 150 mg of amine dextran 3 is solubilized in 0.1M sodium carbonate-bicarbonate pH 8.6 buffer at 25 mg/ml using brief sonication and stirring at ambient temperature for 30 minutes. Solid DOTA-NHS (48 mg, 0.063 mmol) is charged to the amine dextran solution and allowed to stir at room temperature for 12 hours. The reaction is washed 3 times by diluting in 0.1M aqueous sodium carbonate and concentrating via 3 kDa MWCO ultrafiltration to remove free DOTA followed by concentration with purified water until the filtrate runs a neutral pH. The retentate product solution is frozen and lyophilized providing an off-white foam. The total DOTA in 4b is determined by spectrophotometric iron-chelation assay at 380 nm and free (unbound) DOTA by HPLC. 93 mg, 1.9 DOTA per dextran chain.

The final step for the synthetic preparation of DTPA-mannose dextran (tilmanocept 5a) and its DOTA counterpart 5b in examples 1 and 2 involve the addition of mannose to the dextran chain via amidate linkages which does not increase polydispersity and the procedure has been previously described (Scheme 1).

Analysis of Uniformly Defined Molecular Weight DTPA and DOTA Mannose Dextrans 5a/5b: Dextran constructs 5a and 5b prepared in examples 1 and 2 were fractionated on a series of MWCO Amicon® Ultra-15 centrifugal filters to obtain a semi-quantitative Mw distribution profile. In each study, approximately 100 mg of lyophilized tilmanocept product was solubilized in 12 ml of purified water and loaded onto the top of a pre-washed 100 kDa MWCO spin-filter. The material was centrifuged at 3250×g in an Eppendorf A-4-62 rotor for 15-40 minutes as minimally required for a final retentate volume of 0.5 ml above the membrane. The fall-through (filtrate) was transferred to a vial and 12 ml of purified water added to the retentate on the top of the spin-filter. The centrifugation was repeated a second and third time, retaining the filtrate in 3 separate vials. The retentate that had not passed through the membrane was transferred to a 4th vial quantitatively using purified water rinses. The vials were then frozen and lyophilized to determine the amount of material in the fall-through vials and retentate. The lyophilized fall-through material was subsequently solubilized in 12 of purified water and transferred to the top of a pre-washed 50 kDa MWCO filter and the centrifugation procedure repeated as above. In this way, a known amount of construct is fractionated into retentate pools of decreasing MW by passing through a 100, 50, 30, 10 and 3 kDa MWCO centrifugal filters.

Figure 1B:
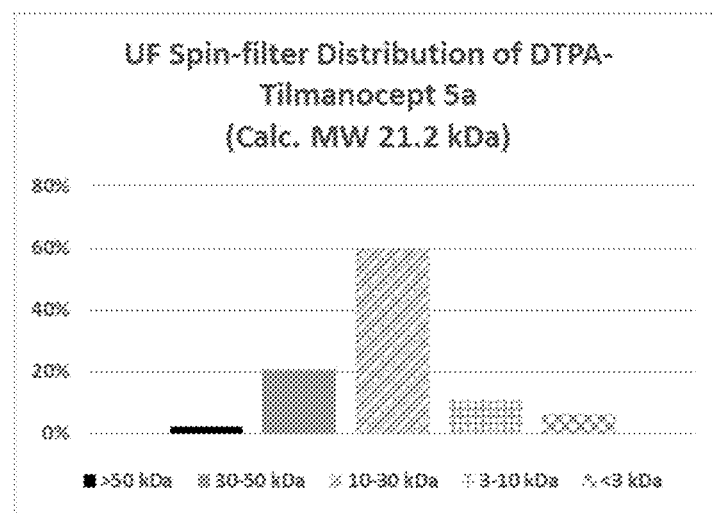
FIG. 1b shows the spin-filter distribution of DTPA-tilmanocept prepared according to certain embodiments of the instantly disclosed process.
Figure 1C:
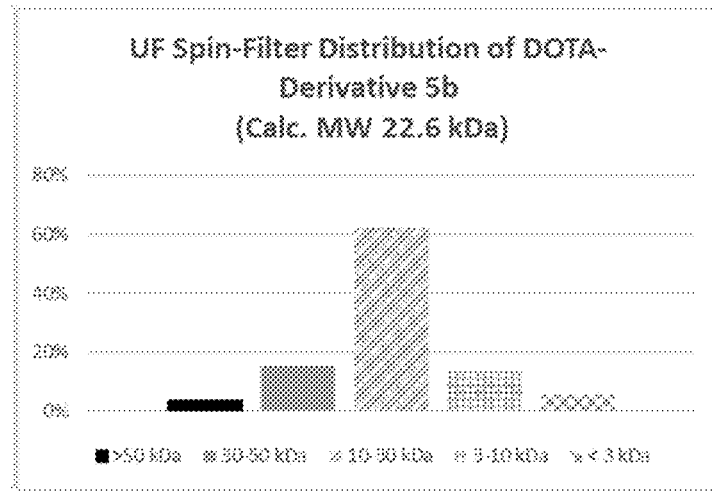
FIG. 1c shows spin-filter distribution of DOTA-tilmanocept prepared according to certain embodiments of the instantly disclosed process.

FIGS. 1 a-c show the series of collected retentates and final fall-through for tilmanocept 5a prepared using the DTPA penta-acid reagent for addition to amine dextran (FIG. 1a) and DTPA-tilmanocept and the DOTA derivative 5b prepared using the mono-activated NHS ester of the chelating agent as described in this disclosure (FIG. 1b and FIG. 1c). The material in FIG. 1a depicts a close to ideal case and was selected as an example of very low polydispersity after activation of unprotected DTPA with IBCF, where higher levels of oligomeric material above 50 kDa is typically observed. Although this 5a batch was successfully prepared with low PDI, the Mw is skewed higher than calculated. In comparison, the constructs synthesized in Examples 1 and 2 of this disclosure utilizing mono-activated DTPA/DOTA (FIGS. 1a and 1b) are much less disperse, with over 60% of the retentate collected bracketing the calculated/targeted Mw range. This study shows that the new method for appending metal-chelators to amine dextran is vastly superior to the current tilmanocept processing step 3 (Scheme 1), delivering a uniform Mw distribution that is only dependent on the inherent polydispersity of the starting dextran, and not the efficiency of chemical addition of the chelating agent.

Example 3

Figure 2:
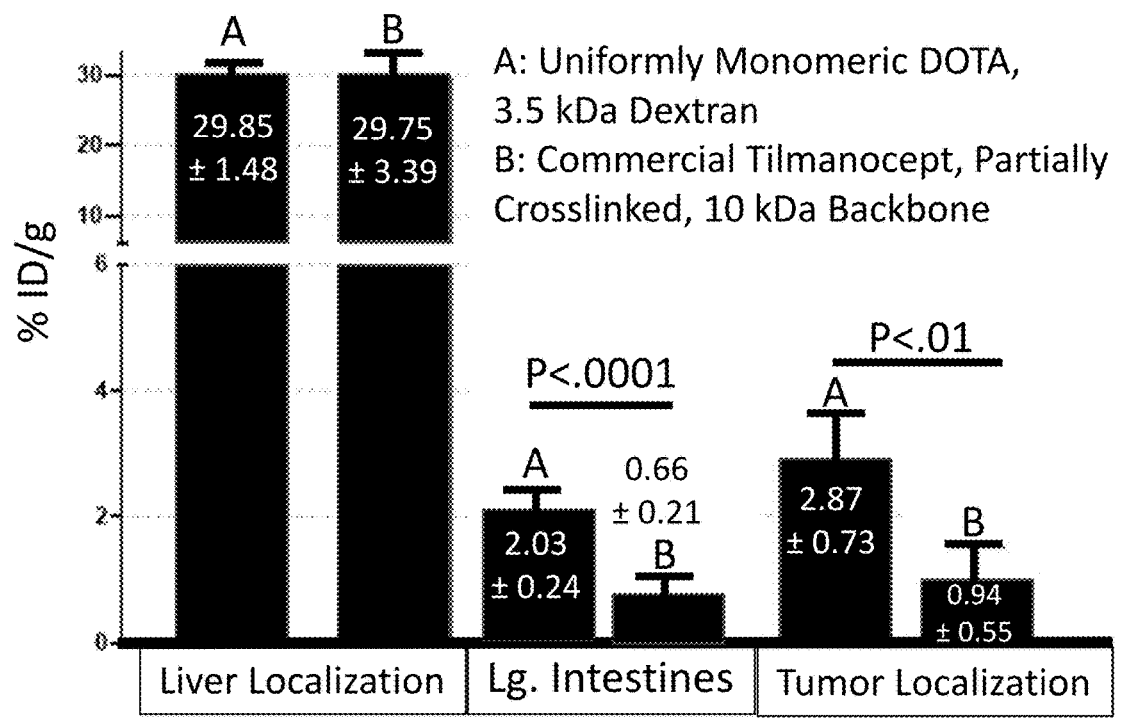
FIG. 2 shows data comparing organ or tumor localization of a non-crosslinked mannosylated dextran construct with a DOTA chelator built on 3.5 kDa dextran backbone and labeled with [68]Ga (calculated Mw=8.7 kDa) and Tilmanocept (10 kDa dextran backbone) with a DTPA chelator labeled with [99m]Tc (measured Mw=37.5 kDa).

A mannosylated dextran construct carrying a DOTA chelator was synthesized according to the presently disclosed methods starting with a 3.5 kDa dextran backbone. The final construct had a calculated Mw of 8.7 kDa. This construct was labeled with [68]Ga. Tilmanocept (10 kDa dextran backbone carrying a DTPA chelator) was prepared by the method described in the 990 patent. This construct had an observed Mw of 37.5 kDa and a calculated Mw of ≈ 20 kDa indicating that a portion of the molecules were crosslinked species. Tilmanocept was labeled with [99m]Tc. These constructs were injected intravenously (IV) into Balb/c mice that had been implanted with CT27 syngeneic tumors. Syngeneic tumors contain numerous CD206+ tumor associated macrophages (TAMs). In addition, CD206+ macrophages occur normally in most tissues of the body including the large intestine. The liver contains large numbers of macrophage-like CD206+ Kupffer cells which are exposed directly to the blood flow providing the injected mannosylated dextrans with unobstructed access to the CD206 receptors expressed by these cells. In most tissues and in tumors, mannosylated dextrans must exit the blood flow and penetrate into the tissues or tumors to encounter CD206 expressing cells (mostly macrophages), Four animals were injected with each labeled construct. Animals were imaged by PET/CT ($^{68}$Ga) or SPECT/CT ($^{99m}$Tc) approximately 1 hour after injection. Standard image analyses determined the amount of the injected dose that localized to each organ or tumor that was then expressed as the percent of the injected dose per gram of tissue (% ID/g) that had localized to the respective organ or tumor as shown in FIG. 2. In FIG. 2, the % ID/g that had localized to the liver was nearly the same for both constructs. This was expected because there are no barriers separating the mannosylated dextrans from CD206 on Kupffer cells. However, for the large intestine and the CT26 tumors, the mannosylated dextrans had to exit the blood flow and penetrate the respective tissues in order to encounter a CD206+ macrophage and localize. As shown in FIG. 2, the non-crosslinked DOTA construct (Mw 8.7 kDa) had significantly greater localization (≈3×) than the crosslinked construct with a Mw of 37.5 kDa. FIG. 2 shows the percent of injected dose per gram (% ID/g) localization of mannosylated dextrans in Balb/c mice with CT26 syngeneic tumors. These tumors contain CD206+ tumor associated macrophages (TAMs). A: a non-crosslinked mannosylated dextran construct with a DOTA chelator built on 3.5 kDa dextran backbone and labeled with [68]Ga (calculated Mw=8.7 kDa). B: Tilmanocept (10 kDa dextran backbone) with a DTPA chelator labeled with [99m]Tc (measured Mw=37.5 kDa).

What is claimed is:

1. A method for conjugating a metal chelating agent to a functionalized dextran comprising:
   reacting a chelator with an aminated dextran backbone, wherein the chelator comprises a plurality of carboxylic acid groups, wherein only one carboxylic acid group is activated to form a chelator-dextran complex, and wherein the additional carboxylic acid group(s) are each conjugated to a protecting group;
   wherein the dextran-chelator complex is substantially free of intra- or intermolecular crosslinking.

2. The method of claim 1, wherein the functionalized dextran is an amine dextran, an alkynyl dextran, or a thiol dextran.

3. The method of claim 2, wherein the functionalized dextran is an amine dextran.

4. The method of claim 3, wherein the one and only one carboxylic acid group on the chelating agent is derivatized as a N-hydroxysuccinimide (NHS) ester.

5. The method of claim 1, wherein the chelator is 1,4,7,10-tetraazacyclododecane-1,4,7,10-tetraacetic acid (DOTA).

6. The method of claim 1, wherein only the one carboxylic acid group is available for activation after the additional carboxylic acid group(s) are each conjugated to a protecting group.

7. The method of claim 1, further comprising removing the protecting groups conjugated to the additional carboxylic acid group(s) from the chelator-dextran complex.

8. The method of claim 1, wherein the protecting groups are chosen from a list consisting of t-butyl esters, benzyl esters, phenyl esters, allyl esters, silyl esters, methyl esters, ortho esters, and oxazolines.

9. The method of claim 8, wherein the protecting groups are t-butyl groups.

10. The method of claim 1, wherein the chelator is diethylenetriaminepentaacetic acid (DTPA).

11. The method of claim 1, wherein prior to reacting the chelator with the aminated dextran backbone, the chelator is synthesized by conjugating the additional carboxylic acid group(s) to the protecting groups, resulting in the only one carboxylic acid group being active to form a mono-NHS-chelator.

12. The method of claim 11, wherein each of the protecting groups is removed, prior to reaction with the dextran backbone.

13. The method of claim 12, wherein the chelator is DTPA.

14. The method of claim 13, wherein the protecting groups are chosen from a list consisting of: t-butyl esters, benzyl esters, phenyl esters, allyl esters, silyl esters, methyl esters, ortho esters, and oxazolines.

15. The method of claim 14, wherein the protecting groups are t-butyl groups.

16. A method for synthesizing an amine dextran comprising:
   a. reacting a chelator with an aminated dextran backbone, wherein the chelator comprises a plurality of carboxylic acid groups, each conjugated to a protecting group with the exception of only one carboxylic acid derivatized as a single activated mono-N-hydroxysuccinimide (NHS) ester, to form a chelator-dextran complex;
   b. removing the protecting groups from each of the plurality of carboxylic acid groups; and
   c. adding a plurality of mannose moieties to the chelator dextran complex through amidate linkage to the dextran backbone.

17. The method of claim 16, wherein the chelator is DTPA or DOTA.

18. The method of claim 17, wherein the protecting groups are chosen from a list consisting of: t-butyl esters, benzyl esters, phenyl esters, allyl esters, silyl esters, methyl esters, ortho esters, and oxazolines.

19. The method of claim 18, wherein the protecting groups are t-butyl groups.

* * * * *